United States Patent [19]

Clingman, Jr. et al.

[11] Patent Number: 5,224,776
[45] Date of Patent: Jul. 6, 1993

[54] INSTRUMENT AND METHOD FOR HEATING VALUE MEASUREMENT BY STOICHIOMETRIC COMBUSTION

[75] Inventors: William H. Clingman, Jr., University Park; Lyn R. Kennedy, Ovilla, both of Tex.

[73] Assignee: Precision Measurement, Inc., Duncanville, Tex.

[21] Appl. No.: 752,432

[22] PCT Filed: Feb. 24, 1989

[86] PCT No.: PCT/US89/00778
§ 371 Date: Aug. 15, 1991
§ 102(e) Date: Aug. 15, 1991

[51] Int. Cl.⁵ ............................................. G01N 25/22
[52] U.S. Cl. ......................................... 374/36; 374/37
[58] Field of Search .................. 374/36, 37, 31; 73/16

[56] References Cited

U.S. PATENT DOCUMENTS

| | | | |
|---|---|---|---|
| 3,777,562 | 12/1973 | Clingman, Jr. | 374/37 |
| 4,062,236 | 12/1977 | Clingman, Jr. | 374/37 |
| 4,125,018 | 11/1978 | Clingman, Jr. | 374/37 |
| 4,163,388 | 8/1979 | November | 374/37 |
| 4,351,614 | 9/1982 | Garnier | 374/37 |
| 4,359,284 | 11/1982 | Kude et al. | 374/37 |
| 4,380,400 | 4/1983 | Searle | 374/37 |
| 4,386,858 | 6/1983 | Kude et al. | 374/37 |
| 4,396,299 | 8/1983 | Clingman, Jr. et al. | 374/37 |
| 4,415,278 | 11/1983 | Szonntagh | 374/37 |
| 4,511,262 | 4/1985 | Arcara | 374/37 |
| 4,632,572 | 12/1986 | Kude et al. | 374/37 |

Primary Examiner—William A. Cuchlinski, Jr.
Assistant Examiner—Diego F. F. Gutierrez
Attorney, Agent, or Firm—Johnson & Gibbs

[57] ABSTRACT

A method and apparatus for determining the calorific value of a first combustible gas involves mixing the first combustible gas with a second combustible gas having a known calorific value and with a combustion supporting gas and burning the resulting mixture, detecting a property of the burning mixture indicative of whether the burning occurred at the stoichiometric point, adjusting the relative flow rates of the first and second combustible gases and the combustion supporting gas so that said burning occurs substantially at the stoichiometric point or at a selected offset from that point, and ascertaining the volume ratios of the gases at the adjusted flow rate to produce a value proportional to the overall calorific value of the mixture of the first and second combustible gases. Based on the foregoing, the contribution to the overall calorific value made by the second combustible gas having a known calorific value can be deleted to yield the calorific value of the first combustible gas.

14 Claims, 1 Drawing Sheet

INSTRUMENT AND METHOD FOR HEATING VALUE MEASUREMENT BY STOICHIOMETRIC COMBUSTION

BACKGROUND OF THE INVENTION

1. Field of the Invention

This invention relates to apparatus and methods for measuring the heating value of gaseous fuels and, more particularly, to apparatus and methods for measuring the heating value of gaseous fuels having low heating values.

2. History of the Prior Art

The calorific value of a combustible gas has been defined as the quantity of heat in British Thermal Units (BTU) which is released when one standard cubic foot of gas is completely oxidized at a temperature of 60° F. and any water produced by oxidation is in the liquid state. When the gas is a hydrocarbon or a mixture of hydrocarbons, the oxidation products of complete oxidation are carbon dioxide and water; and when one standard cubic foot of the gas is mixed with a sufficient quantity of oxygen at 60° F. to completely oxidize the gas, oxidation is carried out and the products thereof, carbon dioxide and water, are cooled to 60° F. and all water is condensed to liquid state. The total heat given off, including the heat transferred in cooling the products and in condensing all of the water, is the calorific value of the gas.

Calorific value so defined is used extensively in industry as a measure of the quality of a gas or other fuel. If a gas is to be fed to a burner, the proper operation of the latter is often highly dependent upon calorific value whereby it is essential to control such value within narrow limits. Accordingly, it is common practice for suppliers and users of combustible gas to monitor the calorific value thereof.

Since the calorific value of a combustible gas depends only on its chemical composition, that value can be determined by a complete chemical analysis of the gas if the calorific value of each of its constituents is known. However, this method is time-consuming and impractical for continuously monitoring the calorific value.

Many standard methods for measuring calorific value involve mixing and burning a known volume of a combustible gas with an excess of oxygen-containing or combustion-supporting gas, transferring the resultant heat to a heat absorbing fluid and measuring the quantity of heat transferred. The conditions for these operations would ideally be the same as in the above definition of calorific value. Any deviation from these conditions will cause the resultant heat transferred per standard cubic foot of combustible gas in the measurement to be different from the calorific value.

In practice, it is difficult to maintain the rigid conditions required for correct measurement. Part of this difficulty stems from the initial temperatures of the combustible and oxygen-containing gases seldom, if ever, being 60° F. Also, the temperature of the combustion products after heat transfer is not 60° F. and, usually, is higher than the initial temperature of the gases. The water produced is seldom condensed to the liquid state and the heat absorbing fluid never absorbs all of the heat transferred from the combustion products, since some heat is always lost by radiation and conduction.

Each of the foregoing deviations is a source of measurement error and correction thereof requires complicated, expensive apparatus and, often, special environmental control.

In response to the above, methods of and means for measuring the calorific value of combustible gases which do not depend upon measuring the amount of heat released in combustion, which are not affected by the errors discussed above, which are capable of continuous operation, and which are not affected by ambient temperature and other varying environmental factors have been developed. One such method and means is disclosed in U.S. Pat. No. 3,777,562 to William H. Clingman, Jr. Briefly, Clingman teaches burning a mixture of a combustible gas and a combustion supporting gas in one or more flames, monitoring the temperature or temperatures of the burned gases, and adjusting the volume ratio of the combustion-supporting gas to the combustible gas so as to maintain the temperature or the average of the temperatures at substantially maximum (i.e., at the stoichiometric point). Because, as taught by Clingman, the volume ratio of the gases which produces the maximum temperature (i.e., the volume ratio at the stoichiometric point) varies substantially directly with the calorific value of the combustible gas, the calorific value of the combustible gas may be determined.

"Stoichiometric combustion" instruments, such as that invented by Clingman and described above, are both accurate and rapid in operation when they can be employed. However, they can only be employed when the gas being analyzed will form a combustible mixture with air. In certain situations, such as those involving flares, it is often necessary to measure gases with low heating values, e.g., 100–200 BTU/scF. These gases may not burn in a premixed flame (although they may burn in a diffusion fed flame, and are in that sense combustible); thus, the heating value of these gases may not be measured by the "stoichiometric combustion" (e.g., Clingman) apparatus, instruments, and methods described above. Additionally, the "stoichiometric combustion" apparatus, instruments, and methods described above always have limited ranges. This is because there is a limited air-fuel ratio for which a flame will be stable in a given burner.

SUMMARY OF THE INVENTION

In accordance with the present invention, a method and apparatus for determining the calorific value of a first combustible gas involves mixing the first combustible gas with a second combustible gas having a known calorific value and with a combustion supporting gas and burning the resulting mixture, detecting a property of the burning mixture indicative of whether the burning occurred at the stoichiometric point, adjusting the relative flow rate of the first and second combustible gases and the combustion supporting gas so that the burning occurs substantially at the stoichiometric point or at a selected offset from that point, and ascertaining the volume ratios of the gases at said adjusted flow rates to produce a value proportional to the overall calorific value of the mixture of the first and second combustible gases. Based on the foregoing, the contribution to the overall calorific value made by the second combustible gas having a known calorific value can be deleted from the volume ratios to yield a calorific value of the first combustible gas.

One instrument and method according to the present invention involves performing adjustment of flow rates by holding the flow rates of the first combustible and the combustion supporting gas substantially fixed and adjusting the flow rate of the second combustible gas. Another instrument and method according to the present invention involves performing adjustment by mixing the two combustible gases together in selected ratio and adjusting the flow rate of the combustion supporting gas.

Accordingly, an object of the present invention is to provide an apparatus and method for measuring the heating value of a gas that is especially suitable for use in control situations.

Another object of the present invention is to provide an apparatus and method capable of continuously measuring heating value over a wide range e.g., 0–1800 BTU/scF.

Yet another object of the present invention is to provide a method and apparatus for measuring the heating values of gases (e.g., 100 BTU/scF mixture of methane with nitrogen) that would be, by themselves, not combustible when premixed with air.

Other objects, advantages and novel features of the present invention will become apparent from the following detailed description of the invention when considered in conjunction with the accompanying drawing wherein:

BRIEF DESCRIPTION OF THE DRAWING

The sole.

DETAILED DESCRIPTION OF THE INVENTION

Figure 1:
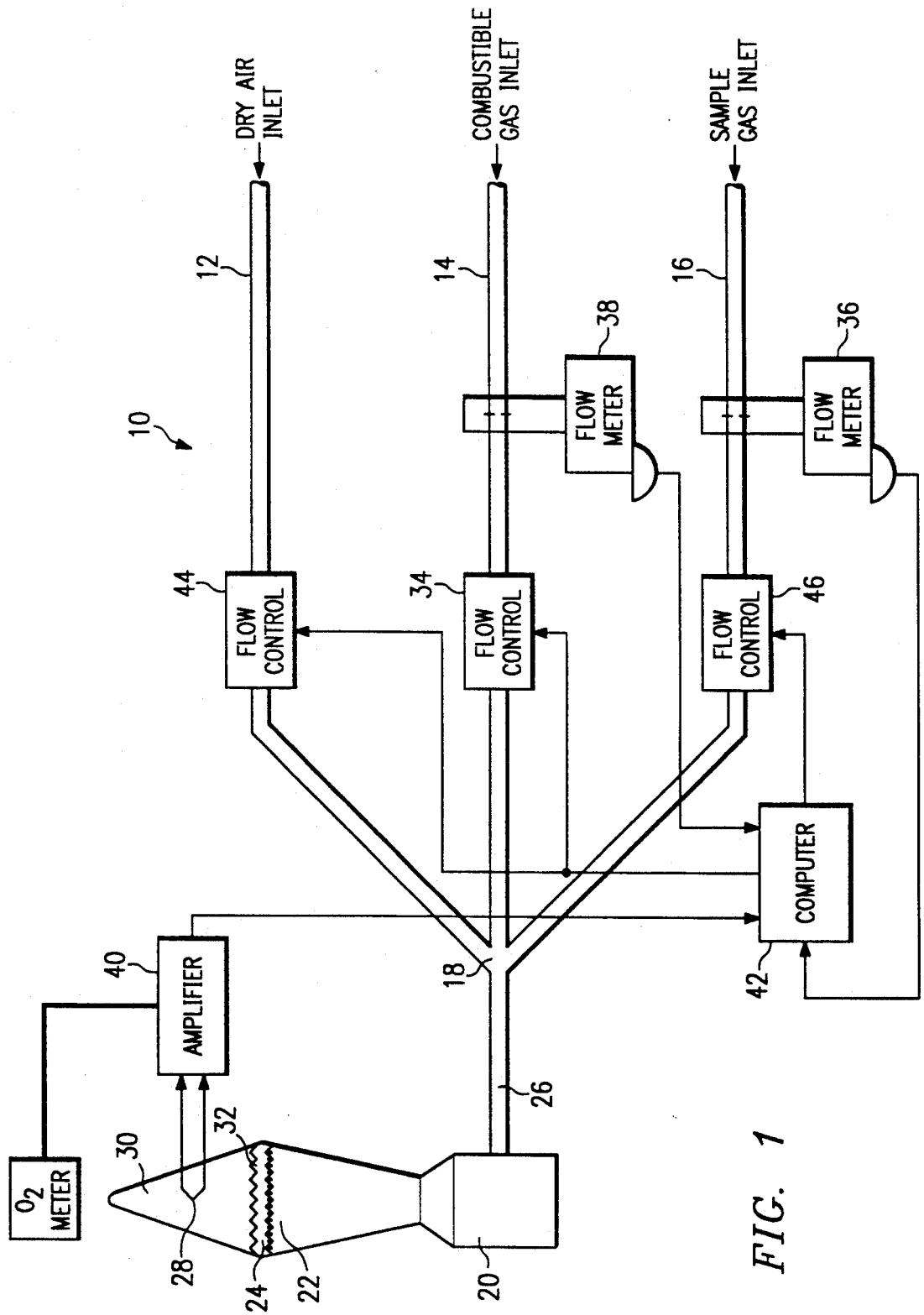
FIG. 1, is a diagrammatic view illustrating a preferred embodiment of the present invention.

A preferred method for measuring the heating value of a gas can be best understood by reference to FIG. 1, wherein a suitable apparatus 10 is illustrated diagrammatically. For convenience, combustion-supporting or oxygen containing gas will be referred to as "dry air" or "air" with the understanding that any suitable gas is included within this designation. A gas with a known heating value will be referred to as a "combustible gas" or "second combustible gas having a known calorific value". Propane or methane would be suitable combustible gases; a number of other gases, well known to those skilled in the relevant art, would also be suitable combustible gases. Finally, the gas to be measured by the apparatus of the present invention will be referred to by the term "sample gas" or "first combustible gas."

Basic elements of apparatus 10 are lines 12, 14, 16 for allowing flow of dry air, combustible gas, and sample gas, respectively, into apparatus 10. At point 18, lines 12, 14, and 16 converge; at this point, any gases flowing through lines 12, 14 and 16 will be mixed.

Apparatus 10 also includes a means for burning, which is shown in FIG. 1 as a flame using burner 20 having a top 22. Burner 20 has a flame supporting grid 24 at its outlet and line 26, which is connected to mixing point 18, at its inlet.

Still further, apparatus 10 includes a means for determining when the mixed gases input into burner 20 are essentially at their stoichiometric point. In FIG. 1, this means is shown as a thermocouple 28. Thermocouple 28 is disposed within a large flame 30 which results when, in the case of many carbon-containing fuels, the carbon monoxide combustion product burns and mixes with ambient air. In any event, as shown by reference numeral 32, a large number of small flames or flamelets emanate from grid 24 upon burning of mixed gas(es) and air. Those skilled in the art know that maximum flame temperature occurs essentially at the stoichiometric point of burning mixed gas and air; thus, those skilled in the art will readily appreciate that by serving as a means for indicating when flame 30 and/or flamelet 32 temperature is at its maximum, an input mixture of air and gas or air and gases is essentially at its stoichiometric point.

As an alternative means for determining the stoichiometric point, an oxygen meter 29 may be used instead of (or as a supplement to) thermocouple 28 in apparatus 10. Change in oxygen content of combusted gases is maximized for a fixed incremental change in mixture ratio. This maximum change occurs at the stoichiometric point. Accordingly, oxygen meter 29 may be employed to determine the point at which oxygen content of combusted gases is at a minimum: that point will be the stoichiometric point.

At this point, sufficient elements have been described to describe exercise of the method of the present invention.

Briefly, a preferred method of the present invention involves determining, for a fixed air flow, the stoichiometric energy flow of a combustible gas, both with and without a measured volumetric flow of sample gas entering the combustion zone. The difference between the two energy flows of the combustible gas divided by the known volumetric flow of sample gas is the heating value of the sample gas. In the practice of such method it does not necessarily matter in what order or amount the three elements of the mixture are combined so long as the first and second combinations reach stoichiometric points as described. Further details concerning the present invention are set forth below. For clarity and convenience, in the ensuing description the combustible gas will be referred to simply as propane and the following letters and subscripts will be used as defined:

$F_s$ = volumetric flow of the sample gas
$F_p$ = volumetric flow of propane
$E_s$ = energy flow of the sample gas
$E_p$ = energy flow of propane
$E_a$ = equivalent air energy flow
$C_p$ = heating value of the propane
$C_s$ = heating value of the sample gas During operation of the present invention a fixed amount of dry air is mixed with propane and burned in burner 20. Via flow control 34 the amount of propane is adjusted until the mixture of dry and air propane is essentially at the stoichiometric point. This can be accomplished by maximizing flame temperature as detected by thermocouple 28.

After the propane/dry air mixture is at its stoichiometric point, sample gas is added to the gaseous mix. The stoichiometric combustion principle implies that the total energy flow into burner 20 (i.e., the sum of the sample gas and propane energy flows) is approximately equal to the equivalent energy flow of air when it is in proportion to propane alone. The equivalent air energy flow, i.e., $E_a$, can be determined periodically by titrating the constant air flow with propane under conditions of no sample gas flow.

In apparatus 10 the volumetric flows of the sample gas ($F_s$) and propane ($F_p$) may be measured using conventional flow meters 36 and 38 respectively, or by another other suitable, known method for measuring flow. As previously indicated $$E_a = E_p + E_s. \tag{1}$$

Additionally $$E_p = F_p \cdot C_p. \quad (2)$$

and $$E_s = F_s \cdot C_s. \quad (3)$$

Substituting $F_p \cdot C_p$ for $E_p$ in equation (1) leads to $$E_a = F_p \cdot C_p + E_s. \quad (4)$$

Rearranging terms leads to $$E_s = E_a - F_p \cdot C_p. \quad (5)$$

Substituting $F_s \cdot C_s$ for $E_s$ in equation (5) leads to $$F_s \cdot C_s = E_a - F_p \cdot C_p. \quad (6)$$

Dividing both sides of the equation by $F_s$ results in $$C_s = (E_a - F_p \cdot C_p)/F_s. \quad (7)$$

Equation (7) provides a basis for calculating heating value. $C_p$ is known from the quality of the propane being used; $F_p$ and $F_s$ are easily measured using flowmeters 38, 36; and $E_a$ is equivalent to $F_p' \cdot C_p$ where $F_p'$ is the volumetric propane flow with no sample gas flow.

Referring again to FIG. 1, it may be seen that a preferred embodiment of the present invention may also include a computer 42 for apparatus 10 control. Signals from thermocouple 28 (and/or oxygen meter 29) indicating flame temperature (and/or indicating the oxygen content of the combusted gases) may be fed through an amplifier 40 (or perhaps even directly) to computer 42, which may be programmed to maximize that temperature (and/or maximize rate of oxygen content change) by exercising control on propane flow via flow control 34. Computer 42 may also be enabled to exercise some control over air and sample gas flows via flow controls 44 and 46, respectively.

The upstream air flow and sample gas flow are set so that the two flows produce a mixture that is always lean. The mixture must be lean for the highest sample gas heating value that is to be measured and for all lower heating values. The mixture must also be lean for pure hydrogen. This has a heating value of only about 330 BTU/scF compared to 1012 BTU/scF for methane. Because of the low density of the hydrogen, however, much more of this gas will flow into the combustion zone than for a hydrocarbon fuel. This is particularly true where the latter is diluted with a high density gas such as carbon dioxide.

A typical setting for maximum range might be 1200-1800 BTU/scF for use in a refinery or chemical processing plant. In some applications, however, the maximum range would be lower as further described below. In the field apparatus 10 can produce a continuous measurement of $C_s$ that can be used for control purposes. If the sample gas is a mixture of inert gas and paraffin hydrocarbons then the stoichiometric combustion theory implies that the measurement will be exact. If the sample contains hydrogen then there will be an error up to 80 BTU/scF for pure hydrogen. Provision can be made in the instrument (e.g., in a program in computer 42) to partially correct for such errors if the composition range is known in advance. In any case, for most control applications the accuracy will be sufficient.

Numerous modifications and variations are possible in light of the above teachings. For example, as discussed in the Summary of the Invention section above, an alternate embodiment of the invention could involve performing adjustment by mixing two combustible gases together and adjusting flow rate of a combustion supporting gas. Other embodiments are possible. In embodiments of the present invention all three elements could be combined at the same time and the respective flowrates adjusted in order to burn the mixture at its stoichiometric point so that the calorific value of the sample gas can be determined. It is essential only that values of sufficient parameters discussed herein be derived to allow calculation of the ultimate calorific value of the sample gas. It is therefore to be understood that within the scope of the appended claims, the invention may be practiced otherwise than as specifically described.

We claim:

1. A method for determining the calorific value of a first combustible gas comprising:
   mixing said first combustible gas with a second combustible gas having a known calorific value and with a combustion supporting gas and burning the resulting mixture;
   detecting a property of the burned mixture indicative of whether said burning occurred at essentially the stochiometric point;
   adjusting the relative flow rates of said first and second combustible gases and said combustion supporting gas so that said burning occurs substantially at said stoichiometric point or at a selected offset from said point;
   ascertaining the volume ratios of said gases at said adjusted flow rates to produce a value proportional to the overall calorific value of said mixture of said first and second combustible gases; and
   deleting from said ratios the contribution to said overall calorific value made by said second combustible gas having a known calorific value, to yield the calorific value of said first combustible gas.

2. A method in accordance with claim 1 in which said indicative property is temperature, which is substantially maximized at the stoichiometric point.

3. A method in accordance with claim 1 in which said indicative property is change of oxygen content in the combusted gases with fixed changes in the mixture ratio, which change in oxygen content is substantially maximized at the stoichiometric point.

4. A method in accordance with claim 1 in which said adjustment of flow rates is performed by holding the flow rates of said first combustible gas and said combustion supporting gas substantially fixed and adjusting the flow rate of said second combustible gas.

5. A method in accordance with claim 1 in which said adjustment is performed by first mixing said two combustible gases together in selected ratio and adjusting the flow rate of said two-gas mixture with respect to the flow rate of said combustion supporting gas.

6. An apparatus for determining the calorific value of a first combustible gas comprising:
   means for mixing said first combustible gas with a second combustible gas having a known calorific value and with a combustion supporting gas and burning the resulting mixture;

means for detecting a property of the burned mixture indicative of whether said burning occurred at the stoichiometric point;

means for adjusting the relative flow rates of said first and second combustible gases and said combustion supporting gas so that said burning occurs substantially at said stoichiometric point or at a selected offset from said point; and means for ascertaining the volume ratios of said gases at said adjusted flow rates to produce a value proportional to the overall calorific value of said mixture of said first and second combustible gases; whereby the contribution to said overall calorific value made by said second combustible gas having a known calorific value can be deleted from said ratios to yield a calorific value of said first combustible gas.

7. An apparatus as recited in claim 6, wherein said indicative property is temperature, which is substantially maximized at the stoichiometric point.

8. An apparatus as recited in claim 6, wherein said indicative property is change of oxygen content in the combusted gases with changes in the mixture ratio, which change in oxygen content is substantially maximized at the stoichiometric point.

9. An apparatus as recited in claim 6, wherein said adjustment of flow rates is performed by holding the flow rates of said first combustible gas and said combustion supporting gas substantially fixed and adjusting the flow rate of said second combustible gas.

10. An apparatus as recited in claim 6, wherein said adjustment is performed by first mixing said two combustible gases together in selected ratio and adjusting the flow rate of said two-gas mixture with respect to the flow rate of said combustion supporting gas.

11. An apparatus for determining the heating value per unit volume of a gas, said apparatus comprising:

(a) means for allowing a known volume flow of said gas; and (b) means for determining heating value of said gas at said known volume flow, said means for determining heating value comprising:
  (i) means for allowing flow of a gas with a known heating value per unit volume;
  (ii) means for adjusting flow of said gas with a known heating value;
  (iii) means for mixing said gas with said gas with a known heating value;
  (iv) means for allowing flow of a combustion supporting gas;
  (v) means for mixing said combustion supporting gas and said gas with a known heating value; and
  (vi) means for burning gas; whereby said gas with a known heating value can be adjusted in flow to a set point, said gas can be mixed with said gas with a known heating value, and said gas with a known heating value can be readjusted in flow to said set point.

12. An apparatus as recited in claim 11, wherein said gas with a known heating value is mixed with said combustion supporting gas to form a first mixture, wherein said first mixture is applied to said burning means, and wherein flow of said gas with a known heating value is adjusted so that said first mixture is essentially at the stoichiometric point.

13. An apparatus as recited in claim 12, wherein said gas is mixed with said first mixture to form a second mixture, wherein said second mixture is applied to said burning means and wherein flow of said gas with a known heating value is adjusted so that said second mixture is essentially at the stoichiometric point.

14. An apparatus as recited in claim 13, wherein said means for determining heating value further comprises:
  (vii) means for determining rate of flow of said gas with a known heating value;

whereby a first energy flow rate when said first mixture is essentially at the stoichiometric point can be determined, a second energy flow rate when said mixture is essentially at the stoichiometric point can be determined, and the difference between said first energy flow rate and said second energy flow rate can be calculated.

* * * * *